(12) United States Patent
Yin

(10) Patent No.: US 8,722,713 B2
(45) Date of Patent: May 13, 2014

(54) SYNERGISTIC ANTIMICROBIAL COMPOSITION OF 1,2-BENZISOTHIAZOLIN-3-ONE AND TRIS(HYDROXYMETHYL)NITROMETHANE

(71) Applicant: Dow Global Technologies LLC, Midland, MI (US)

(72) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/104,467

(22) Filed: Dec. 12, 2013

(65) Prior Publication Data

US 2014/0100253 A1    Apr. 10, 2014

Related U.S. Application Data

(62) Division of application No. 13/291,524, filed on Nov. 8, 2011, now Pat. No. 8,680,128.

(60) Provisional application No. 61/415,029, filed on Nov. 18, 2010.

(51) Int. Cl.
*A01N 43/80* (2006.01)
*A61K 31/425* (2006.01)

(52) U.S. Cl.
USPC .......................................... 514/372; 514/373

(58) Field of Classification Search
CPC .... A61K 31/04; A61K 31/047; A61K 31/425
USPC .................................................. 514/372, 373
See application file for complete search history.

(56) References Cited

U.S. PATENT DOCUMENTS

| 6,432,433 B1 | 8/2002 | Winkowski et al. |
| 7,468,384 B2 | 12/2008 | Levy et al. |
| 2008/0004189 A1 | 1/2008 | Smith et al. |

FOREIGN PATENT DOCUMENTS

JP    11130604    5/1999

OTHER PUBLICATIONS

"Product Information: Bi0ban(TM) Ultra Bit 20 LE Antimicrobial (Brand of 1,2-benzisothiazolin-3-one)", http://www.dow.com/ucon/stle2011/pdfs/microbial_lit/BI0BAN_U LTRA_BIT_20_LE_Antimicrobial.pdf, pp. 1-4 (2009).
"Product Information: TRIS NITRO (Brand of TRIS (Hydroxymethyl) Nitromethane) ", http://www.dow.com/PublishedLiterature/dh_003a/0901b8038003aea2.pdf, 1-9 (2002).
Groot, et al., "Formaldehyde-releasers: relationship to formaldehyde contact allergy. Contact allergy to formaldehyde and inventory of formaldehyde-releasers", Contact Dermatitis, vol. 61, pp. 63-85 (2009).

*Primary Examiner* — Yong Chong
(74) *Attorney, Agent, or Firm* — Kenneth Crimaldi

(57) ABSTRACT

A synergistic antimicrobial composition containing 1,2-benzisothiazolin-3-one and tris(hydroxymethyl)nitromethane.

3 Claims, No Drawings

SYNERGISTIC ANTIMICROBIAL COMPOSITION OF 1,2-BENZISOTHIAZOLIN-3-ONE AND TRIS(HYDROXYMETHYL)NITROMETHANE

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature and high pH. Combinations of different antimicrobial compounds are sometimes used to provide overall control of microorganisms or to provide the same level of microbial control at lower use rates in a particular end use environment. For example, U.S. Pat. No. 6,432,433 discloses combinations of 1,2-benzisothiazolin-3-one (BIT) and a formaldehyde adduct, but this reference does not suggest any of the combinations claimed herein. Moreover, there is a need for additional combinations of antimicrobial compounds having enhanced activity to provide effective control of microorganisms. The problem addressed by this invention is to provide such combinations of antimicrobial compounds.

STATEMENT OF THE INVENTION

The present invention is directed to a synergistic antimicrobial composition comprising: (a) 1,2-benzisothiazolin-3-one; and (b) tris(hydroxymethyl)nitromethane (Tris Nitro); wherein a weight ratio of 1,2-benzisothiazolin-3-one to tris(hydroxymethyl)nitromethane is from 12:1 to 1:12.

DETAILED DESCRIPTION OF THE INVENTION

As used herein, the following terms have the designated definitions, unless the context clearly indicates otherwise. The term "antimicrobial compound" refers to a compound capable of inhibiting the growth or propagation of microorganisms, and/or killing microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. Other biocides may be present in the antimicrobial composition.

Preferably, a weight ratio of BIT to Tris Nitro is from 10:1 to 1:12, preferably from 10:1 to 1:10, preferably from 9:1 to 1:12, preferably from 9:1 to 1:10, preferably from 9:1 to 1:9, preferably from 9:1 to 1:8.2. Preferably, the composition is used to prevent growth of anaerobic bacteria, at a weight ratio of the BIT to Tris Nitro from 12:1 to 1:7; preferably from 12:1 to 1:6; preferably from 12:1 to 1:5; preferably from 10:1 to 1:4; preferably from 10:1 to 1:3; preferably from 10:1 to 1:5; preferably from 9:1 to 1:5; preferably from 9:1 to 1:4; preferably from 9:1 to 1:3. Preferably, the composition is used to prevent growth of aerobic bacteria, at a weight ratio of the BIT to Tris Nitro from 1:2 to 1:12; preferably from 1:2 to 1:10; preferably from 1:2 to 1:9; preferably from 1:2 to 1:8.5; preferably from 1:2.5 to 1:10; preferably from 1:2.5 to 1:9; preferably from 1:2.5 to 1:8.5; preferably from 1:2.5 to 1:8.2; preferably from 1:2.9 to 1:8.2.

Preferably, the antimicrobial combination of this invention is useful in oil and gas field injection, produced fluids, fracturing fluids and functional fluids, oil and gas wells, oil and gas operation, separation, storage, and transportation systems, oil and gas pipelines, oil and gas vessels, and fuel. The combination is especially useful in aqueous fluids added to or produced by oil and gas well. The composition also is useful for controlling microorganisms in other industrial water and water containing/contaminated matrixes, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, personal care and household products such as detergent, filtration systems (including reverse osmosis and ultrafiltration systems), toilet bowel, textiles, leather and leather production system, or a system used therewith.

Typically, the amount of the biocide combinations of the present invention to control the growth of microorganisms is from 10 ppm to 5,000 ppm active ingredient. Preferably, the active ingredients of the composition are present in an amount of at least 20 ppm, preferably at least 50 ppm, preferably at least 100 ppm, preferably at least 150 ppm, preferably at least 200 ppm. Preferably, the active ingredients of the composition are present in an amount of no more than 2,000 ppm, preferably no more than 1,000 ppm, preferably no more than 500 ppm, preferably no more than 400 ppm, preferably no more than 300 ppm, preferably no more than 250 ppm, preferably no more than 200 ppm, preferably no more than 100 ppm, preferably no more than 50 ppm. Concentrations mentioned above are in a liquid composition containing the biocide combinations. Biocide concentrations in a high-sulfide and high-temperature environment typically will be higher than in other environments.

The present invention also encompasses a method for reducing, or inhibiting, or preventing microbial growth in the use areas described above, especially in oil or natural gas production operations, by incorporating the claimed biocide combination into the materials.

EXAMPLES

Example 1

Synergistic Effect of BIT and Tris Nitro, Against Anaerobic Bacteria

Inside an anaerobic chamber (Bactron anaerobic chamber), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated anaerobic consortium, mainly SRB, at final bacterial concentrations of $10^6$ to $10^7$ CFU/mL. The aliquots of this contaminated water were then treated with BIT, Tris Nitro, or the BIT/Tris Nitro combinations at different active concentration levels. After the mixtures were incubated at 40° C. for 24 hour, the biocidal efficacy was determined by minimum tested biocide concentration for bacteria kill in the aliquots (MBC). Table 1 summarizes the efficacy of each biocide and their blends, and the Synergy Index* of each combination.

TABLE 1

Biocidal efficacy of BIT, Tris Nitro, BIT/Tris Nitro combination, and Synergy Index

| Ratio of BIT to Tris Nitro (active w/w) | MBC (active ppm) | | Synergy Index* |
|---|---|---|---|
| | BIT | Tris Nitro | |
| 1:0 | 17.3 | 0.0 | |
| 9:1 | 14.8 | 1.6 | <0.87 |
| 3:1 | 13.9 | 4.6 | <0.85 |
| 1:1 | 11.8 | 11.8 | <0.80 |
| 1:3 | 8.1 | 24.2 | <0.71 |
| 1:9 | >8.1 | >73 | NA |
| 0:1 | 0.0 | >100 | |

*Synergy Index = Ca/CA + Cb/CB
Ca: Concentration of biocide A required to achieve a complete bacterial kill when used in combination with biocide B
CA: Concentration of biocide A required to achieve a complete bacterial kill when used alone
Cb: Concentration of biocide B required to achieve a complete bacterial kill when used in combination with biocide A
CB: Concentration of biocide B required to achieve a complete bacterial kill when used alone
Synergy Index
<1: synergy
=1: additivity
>1: antagonism As shown in Table 1, BIT in combination with Tris Nitro had a synergistic effect at an active weight ratio of BIT to Tris Nitro at least from 9:1 to 1:3.

Example 2

Synergistic Effect of BIT and Tris Nitro Against Aerobic Bacteria

A sterile NaCl solution (0.85%) was contaminated with *Psedomonas aeruginosa* ATCC 10145 and *Staphylococcus aureus* ATCC 6538 at final bacterial concentration of ~$10^6$ CFU/ml. The aliquots of this contaminated water were then treated with BIT, Tris Nitro, or the BIT/Tris Nitro combination at different active concentration levels. After the mixtures were incubated at 37° C. for 24 hour, the biocidal efficacy was determined by minimum tested biocide concentration for complete bacteria kill (MBC) in the aliquots. Table 2 summarizes the efficacy of each biocide and their blends, and the Synergy Index of each combination.

TABLE 2

Biocidal efficacy of BIT, Tris Nitro, BIT/Tris Nitro combination, and Synergy Index

| Ratio of BIT to Tris Nitro (active w/w) | Dosage required for complete kill (active ppm) | | Synergy Index |
|---|---|---|---|
| | BIT | Tris Nitro | |
| 1:0 | >25 | 0.0 | |
| 8.1:1 | >25 | >3.1 | NA |
| 2.9:1 | >25.1 | >8.8 | NA |
| 1:1 | 16.3 | 16.3 | <1.29 |
| 1:2.9 | 3.7 | 10.5 | <0.56 |
| 1:8.2 | 1.8 | 14.9 | <0.65 |
| 0:1 | 0.0 | 25.7 | |

As shown in the table 2, BIT in combination with Tris Nitro, had a strong synergistic effect at an active weight ratio of BIT to Tris Nitro at least from 1:2.9 to 1:8.2 and much lower dosages were needed for good aerobic bacterial control when used in combination than used separately.

The invention claimed is:

1. A method for reducing bacterial growth in an aqueous medium; said method comprises adding to the aqueous medium: (a) 1,2-benzisothiazolin-3-one; and (b) tris(hydroxymethyl)nitromethane; wherein a weight ratio of 1,2-benzisothiazolin-3-one to tris(hydroxymethyl)nitromethane is from 9:1 to 1:8.2.

2. The method of claim 1 in which the aqueous medium comprises anaerobic bacteria and the weight ratio is from 9:1 to 1:3.

3. The method of claim 2 in which the aqueous medium comprises aerobic bacteria and the weight ratio is from 1:2.9 to 1:8.2.

* * * * *